(12) United States Patent
Bonilla

(10) Patent No.: US 6,364,862 B1
(45) Date of Patent: Apr. 2, 2002

(54) SINGLE PAD FOR PROVIDING BOTH AN ANESTHETIC AND AN ANTISEPTIC FOR AN INJECTION SITE

(75) Inventor: Daniel Bonilla, 212 Jackson St., Hoboken, NJ (US) 07030

(73) Assignee: Daniel Bonilla, Hoboken, NJ (US)

( * ) Notice: Subject to any disclaimer, the term of this patent is extended or adjusted under 35 U.S.C. 154(b) by 0 days.

(21) Appl. No.: 09/398,930

(22) Filed: Sep. 17, 1999

(51) Int. Cl.⁷ .............................................. A61M 35/00
(52) U.S. Cl. ...................... 604/289; 604/290; 604/304; 602/48
(58) Field of Search ................................ 604/199, 289, 604/290, 304; 602/48–51

(56) References Cited

U.S. PATENT DOCUMENTS

| | | | | |
|---|---|---|---|---|
| 3,624,224 A | * | 11/1971 | Wei | ............................. 424/28 |
| 4,281,650 A | * | 8/1981 | Spiegelberg | ................. 604/304 |
| 4,799,926 A | * | 1/1989 | Haber | ......................... 604/199 |
| 4,988,341 A | * | 1/1991 | Columbus et al. | .......... 604/304 |

* cited by examiner

Primary Examiner—Dennis Ruhl
(74) Attorney, Agent, or Firm—The Invention Company; Dario Santoro

(57) ABSTRACT

A single pad for providing both an anesthetic and an antiseptic for an injection site. The pad includes a first layer of material, a second layer of material, a third layer of material, an antiseptic solution, and an anesthetic solution. The second layer of material overlays the first layer of material. The third layer of material overlays the second layer of material. The antiseptic solution impregnates the first layer of material and cleans the injection site. The anesthetic solution impregnates the third layer of material, anesthetizes the injection site, and is used by merely turning the pad over after the antiseptic solution has been applied.

7 Claims, 1 Drawing Sheet

SINGLE PAD FOR PROVIDING BOTH AN ANESTHETIC AND AN ANTISEPTIC FOR AN INJECTION SITE

BACKGROUND OF THE INVENTION

1. Field of the Invention

The present invention relates to a pad. More particularly, the present invention relates to a single pad for providing both an anesthetic and an antiseptic for an injection site.

2. Description of the Prior Art

Cleansing solutions, such as alcohol, are normally applied to a patient's skin area where certain medical procedures are to be performed, such as insertion of a hypodermic needle for various purposes including administration of medications, blood withdrawal, and initiation of intravenous therapy.

In the past when an injection was to be given, it was common to swab the affected area both before and after the injection. This is usually done by another than the one making injections, or by the injector laying the hypodermic syringe aside while the antiseptic is being applied with swab held in an entirely separate instrument. The need to lay aside the hypodermic syringe and use a separate instrument, such as forceps or the like to apply the antiseptic to the point of injection caused considerably lost time.

When using the hypodermic syringes presently on the market, the physician still has to carry with him when visiting his patients, a bottle of antiseptic liquid, such as either, alcohol or the like as well as a box of absorbent material, such as cotton. Furthermore, every time an injection has to be made, he has to go through several motions in order to sterilize the skin through which the injection is to be made.

All these operations are time consuming and this is rather important, particularly for the physician whose schedule is usually very heavy. Also, it happens from time to time that the physician runs out of either the antiseptic liquid or the absorbent cotton or both, and on such occasions none may be available on site.

Furthermore, the skin area is often not anesthetized to reduce pain from the procedure, since known means for applying anesthetic agents are cumbersome and time consuming.

Numerous innovations for medicinal applicators have been provided in the prior art that will be described. Even though these innovations may be suitable for the specific individual purposes to which they address, however, they differ from the present invention.

FOR EXAMPLE, U.S. Pat. No. 4,243,035 to Barrett teaches a hypodermic syringe and integral antiseptic dispenser, with the syringe having a barrel portion adapted to contain fluid to be injected. A needle is operatively mounted on one end of the barrel portion, and a plunger is located on the other end of the barrel portion, with appropriate manipulation of the plunger bringing about the injection of fluid from the needle. The improvement comprises a presoaked antiseptic dispenser that may be disposed on the barrel portion, with the antiseptic dispenser making it convenient to clean the intended injection site immediately before the injection. The antiseptic dispenser may take the form of a pad carried by the barrel portion of the syringe, or a generally cylindrical pad-carrying member encircling a portion of the needle end of the syringe, or any of a number of related configurations.

ANOTHER EXAMPLE, U.S. Pat. No. 5,690,958 to McGrath teaches a unit dose chlorhexadine gluconate (CHG) applicator wherein a unit dose of the CHG is contained in a hermetically sealed manually crushable glass ampule that has an internal volume not significantly greater than the unit dose volume of the CHG. The CHG in the ampule has an effective shelf life of at least 24 months. The glass ampule of the applicator is preferably protected by a flexible cover to protect the user's hand during manual crushing of the ampule to release the CHG therefrom. In one embodiment of the invention, a cylindrical glass ampule is housed within a tubular, flexible synthetic resin cover which has a porous applicator swab at one end thereof. Upon crushing of the glass ampule, the CHG released therefrom impregnates the swab allowing the user to spread the CHG across an area to be sanitized. In a second embodiment of the invention, a cylindrical glass ampule is received within a semi-cylindrical, open-sided body cover having a flange portion that mounts a sponge-like swab communicating with the interior of the body cover. Opposed integral wing-like gripping members on the ampule permit the user to crush the ampule by squeezing the members toward one another whereupon the CHG is released from the ampule and impregnates the sponge swab. The swab soaked with the CHG antiseptic may be rubbed across an area to be sanitized.

STILL ANOTHER EXAMPLE, U.S. Pat. No. 5,704,906 to Fox teaches a topical anesthetic-cleansing solution and applicator. The anesthetic-cleansing solution comprises an anesthetic agent such as Benzocaine and a cleansing solution such as alcohol. The applicator includes a swab and outer packaging housing the swab in a generally sterile environment. The swab includes an elongated member and an absorbent tip attached to the elongated member. The absorbent tip is impregnated with the anesthetic-cleansing solution. A method is also provided for using the applicator. The method includes the steps of holding a portion of the packaging covering the swab elongated member; removing a portion of the packaging covering the absorbent tip to expose the absorbent tip; and applying the absorbent tip on the patient's skin area to be anesthetized and cleansed.

It is apparent that numerous innovations for medicinal applicators have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a single pad for providing both an anesthetic and an antiseptic for an injection site that avoids the disadvantages of the prior art.

ANOTHER OBJECT of the present invention is to provide a single pad for providing both an anesthetic and an antiseptic for an injection site that is simple and inexpensive to manufacture.

STILL ANOTHER OBJECT of the present invention is to provide a single pad for providing both an anesthetic and an antiseptic for an injection site that is simple to use.

BRIEFLY STATED, YET ANOTHER OBJECT of the present invention is to provide a single pad for providing both an anesthetic and an antiseptic for an injection site. The pad includes a first layer of material, a second layer of material, a third layer of material, an antiseptic solution, and an anesthetic solution. The second layer of material overlays the first layer of material. The third layer of material overlays the second layer of material. The antiseptic solution impregnates the first layer of material and cleans the injection site. The anesthetic solution impregnates the third layer of material, anesthetizes the injection site, and is used by merely turning the pad over after the antiseptic solution has been applied.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
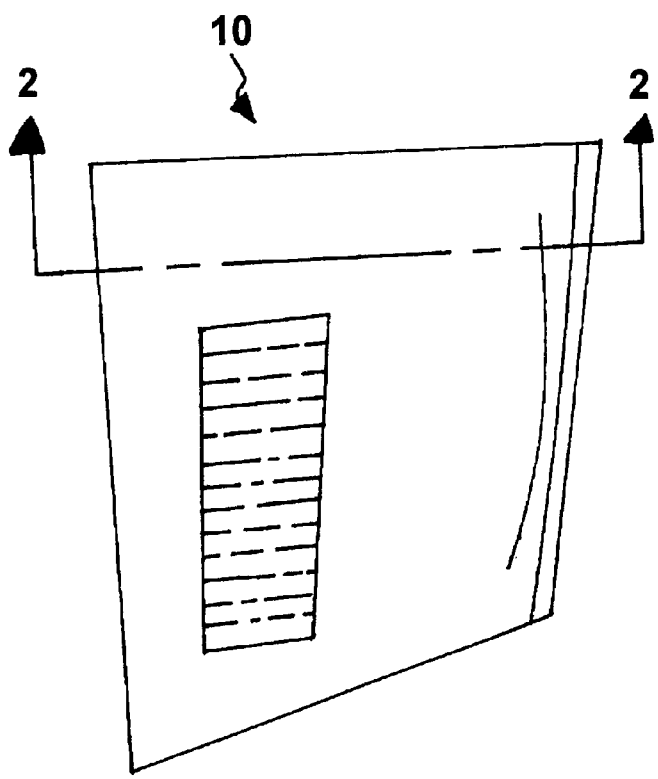
FIG. 1 is a diagrammatic perspective view of the present invention.

LIST OF REFERENCE NUMERALS UTILIZED IN THE DRAWING 10 single pad of the present invention for providing both anesthetic and antiseptic for injection site
12 first layer of material
14 second layer of material
16 third layer of material
18 antiseptic solution for cleaning injection site
20 anesthetic solution for anesthetizing injection site
22 packet

DETAILED DESCRIPTION OF THE PREFERRED EMBODIMENT

Referring now to the figures, in which like numerals indicate like parts, and particularly to FIG. 1, which is a diagrammatic perspective view of the present invention, the single pad of the present invention is shown generally at 10 for providing both an anesthetic and an antiseptic for an injection site.

Figure 2:
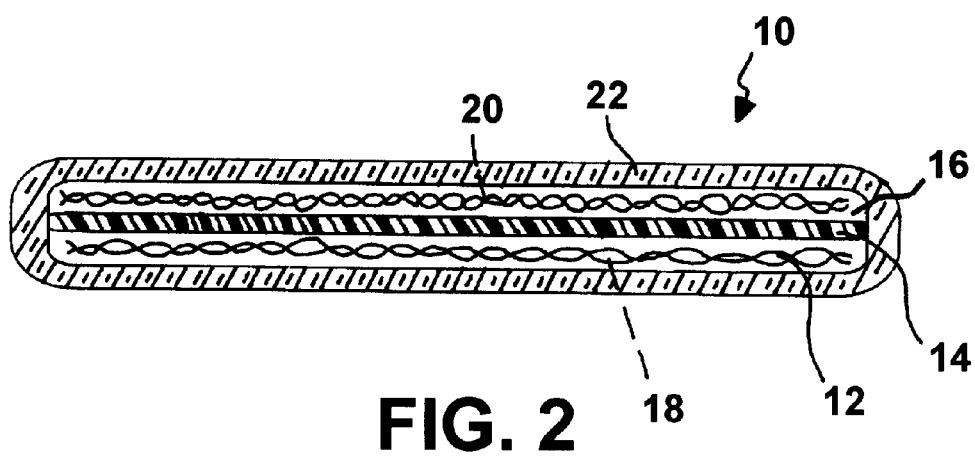
FIG. 2 is an enlarged diagrammatic cross sectional view taken on LINE 2—2 in FIG. 1.

The configuration of the single pad 10 can best be seen in FIG. 2, which is an enlarged diagrammatic cross sectional view taken on LINE 2—2 in FIG. 1, and as such, will be discussed with reference thereto.

The single pad 10 comprises a first layer of material 12, a second layer of material 14 overlying the first layer of material 12, a third layer of material 16 overlying the second layer of material 14, an antiseptic solution 18 impregnating the first layer of material 12 for cleaning the injection site, and an anesthetic solution 20 impregnating the third layer of material 16 for anesthetizing the injection site and being used by merely turning the pad 10 over after the antiseptic solution 18 has been applied.

The pad 10 further comprises a packet 22 vacuumizing an individual pad 10 therein and preserving the antiseptic solution 18 and the anesthetic solution 20.

The first layer of material 12 is cotton, square, and measures 1.5"×1.5".

The third layer of material 16 is cotton, square, measures 1.5"×1.5", and is as thick as the first layer of material 12.

The second layer of material 14 is a plastic barrier that prevents the antiseptic solution 18 and the anesthetic solution 20 from mixing with each other.

The second layer of material 14 is square, measures 1.5"×1.5", and is thinner than each of the first layer of material 12 and the third layer of material 16.

It will be understood that each of the elements described above, or two or more together, may also find a useful application in other types of constructions differing from the types described above.

While the invention has been illustrated and described as embodied in a single pad for providing both an anesthetic and an antiseptic for an injection site, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A single pad for providing both an anesthetic and an antiseptic for an injection site, comprising:
   a) a first layer of material;
   b) a second layer of material overlying said first layer of material;
   c) a third layer of material overlying said second layer of material;
   d) an antiseptic solution impregnating said first layer of material for cleaning the injection site;
   e) an anesthetic solution impregnating said third layer of material for anesthetizing the injection site and being used by merely turning said pad over after said antiseptic solution has been applied; and
   f) a packet vacuumizing an individual said pad therein and preserving said antiseptic solution and said anesthetic solution.

2. The pad as defined in claim 1, wherein said first layer of material is cotton.

3. The pad as defined in claim 1, wherein said first layer of material is square and measures 1.5"×1.5".

4. The pad as defined in claim 1, wherein said third layer of material is cotton.

5. The pad as defined in claim 1, wherein said third layer of material is square, measures 1.5"×1.5", and said third layer of material is as thick as said first layer of material.

6. The pad as defined in claim 1, wherein said second layer of material is a plastic barrier that prevents said antiseptic solution and said anesthetic solution from mixing with each other.

7. The pad as defined in claim 1, wherein said second layer of material is square, measures 1.5"×1.5", and is thinner than each of said first layer of material and said third layer of material.

* * * * *